US010661310B2

(12) United States Patent
Yamamoto et al.

(10) Patent No.: US 10,661,310 B2
(45) Date of Patent: May 26, 2020

(54) ULTRASONIC OSCILLATOR UNIT

(71) Applicant: FUJIFILM Corporation, Tokyo (JP)

(72) Inventors: Katsuya Yamamoto, Ashigarakami-gun (JP); Yasuhiko Morimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 91 days.

(21) Appl. No.: 16/157,533

(22) Filed: Oct. 11, 2018

(65) Prior Publication Data

US 2019/0047021 A1 Feb. 14, 2019

Related U.S. Application Data

(63) Continuation of application No. PCT/JP2017/007403, filed on Feb. 27, 2017.

(30) Foreign Application Priority Data

Apr. 28, 2016 (JP) .................. 2016-091934

(51) Int. Cl.
*B06B 3/04* (2006.01)
*A61B 8/12* (2006.01)
(Continued)

(52) U.S. Cl.
CPC .............. *B06B 3/04* (2013.01); *A61B 1/0011* (2013.01); *A61B 1/00114* (2013.01); *A61B 8/12* (2013.01);
(Continued)

(58) Field of Classification Search
CPC ....... B06B 3/04; A61B 1/0011; A61B 1/0114; A61B 8/445; A61B 8/4494; A61B 8/12;
(Continued)

(56) References Cited

U.S. PATENT DOCUMENTS

2008/0312537 A1 12/2008 Hyuga
2009/0093725 A1 4/2009 Sato et al.
(Continued)

FOREIGN PATENT DOCUMENTS

JP 7-274295 A 10/1995
JP 8-4359 A 1/1996
(Continued)

OTHER PUBLICATIONS

International Preliminary Report on Patentability and Written Opinion of the International Searching Authority(Forms PCT/IB/326, PCT/IB/373 and PCT/ISA/237), dated Nov. 8, 2018 for International Application No. PCT/JP2017/007403, with an English Translation of the Written Opinion.
(Continued)

*Primary Examiner* — Jeffrey M Shin
(74) *Attorney, Agent, or Firm* — Birch, Stewart, Kolasch & Birch, LLP

(57) ABSTRACT

A ultrasonic oscillator unit including an ultrasonic oscillator array in which a plurality of oscillators are arranged in a circular-arc shape; an electrode part that is provided on at least one end surface of the plurality of oscillators perpendicular to a longitudinal direction thereof and that is electrically connected with the oscillators; a backing material layer that is disposed on a rear surface of the ultrasonic oscillator array; and a cable wiring part including a flexible printed wired board. The flexible printed wired board includes a cable connecting part that extends to a lower side of the backing material layer, is separated into a plurality of belt-like pieces, and has, in a comb shape, a plurality of strip-like electrode parts in which at least one electrode pad is linearly disposed in the longitudinal direction of each of the belt-like pieces.

20 Claims, 4 Drawing Sheets

(51) Int. Cl.
*A61B 8/00* (2006.01)
*A61B 1/00* (2006.01)
*H03B 1/02* (2006.01)
*H03B 17/00* (2006.01)
*H05K 1/02* (2006.01)
*H05K 1/18* (2006.01)

(52) U.S. Cl.
CPC ............ *A61B 8/445* (2013.01); *A61B 8/4494* (2013.01); *H03B 1/02* (2013.01); *H03B 17/00* (2013.01); *H05K 1/028* (2013.01); *H05K 1/189* (2013.01)

(58) Field of Classification Search
CPC ........ H05K 1/189; H05K 1/028; H03B 17/00; H03B 1/02
See application file for complete search history.

(56) References Cited

U.S. PATENT DOCUMENTS

2014/0058269 A1   2/2014   Irie
2019/0021696 A1*  1/2019   Morimoto ................ A61B 8/12
2019/0038257 A1*  2/2019   Yamamoto ........... A61B 8/4488

FOREIGN PATENT DOCUMENTS

| | | |
|---|---|---|
| JP | 2001-299755 A | 10/2001 |
| JP | 3802756 B2 | 7/2006 |
| JP | 2008-311700 A | 12/2008 |
| JP | 2009-239976 A | 10/2009 |
| JP | 4445764 B2 | 4/2010 |
| JP | 4980653 B2 | 7/2012 |
| JP | 5399594 B1 | 1/2014 |

OTHER PUBLICATIONS

International Search Report (Form PCT/ISA/210), dated May 30, 2017, for International Application No. PCT/JP2017/007403, with an English translation.

Extended European Search Report, dated Feb. 14, 2019, for corresponding European Application No. 17789044.9.

European Office Action for corresponding European Application No. 17789044.9, dated Oct. 17, 2019.

* cited by examiner

ULTRASONIC OSCILLATOR UNIT

CROSS-REFERENCE TO RELATED APPLICATIONS

This application is a Continuation of PCT International Application No. PCT/JP2017/007403 filed on Feb. 27, 2017, which claims priority under 35 U.S.C § 119(a) to Japanese Patent Application No. 2016-091934 filed on Apr. 28, 2016. Each of the above application(s) is hereby expressly incorporated by reference, in its entirety, into the present application.

BACKGROUND OF THE INVENTION

1. Field of the Invention

The present invention relates to an ultrasonic oscillator unit having an ultrasonic oscillator wiring structure for realizing a small-sized ultrasonic oscillator.

2. Description of the Related Art

Ultrasonic endoscopes are ones in which an ultrasonic observation part is provided at a distal end part of an ultrasonic endoscope with observation of the gallbladder or the pancreas by an alimentary canal as a main purpose. In order to safely insert the ultrasonic endoscope into the alimentary canal, an optical sensor, illumination means, an air supply port, a water supply port, and a suction port in addition to the ultrasonic observation part are provided at the distal end part of the ultrasonic endoscope, similarly to ordinary endoscopes that are not provided with the ultrasonic observation part. For that reason, the external diameter of the distal end part of the ultrasonic endoscope increases, and causes a decrease in the operability of the ultrasonic endoscope and an increase in the burden on a patient into which the distal end part of the ultrasonic endoscope is to be inserted.

Thus, in order to improve the operability of the ultrasonic endoscope and mitigate the burden on the patient, the ultrasonic observation part is required to be small-sized. Thus, in recent years, various proposals, such as improving the workability in wiring task and making the ultrasonic observation part of the ultrasonic endoscope small-sized are made (refer to JP4445764B, JP5399594B, JP1996-004359A (JP-H08-004359A), JP4980653B, and JP3802756B).

JP4445764B discloses an ultrasonic oscillator unit having an ultrasonic oscillator array that has an acoustic matching layer, piezoelectric elements, and a rear surface damping layer; a rigid board electrically connected to the respective piezoelectric elements in the vicinity of a central part of the ultrasonic oscillator array in a width direction thereof; a signal cable bundle including a plurality of signal core wires; and a flexible printed wired board that is interposed between the rigid board and the signal cable bundle to electrically connect both. Moreover, the ultrasonic oscillator array, and the cable bundle and the flexible printed wired board are separate structures, both are connected to each other using thermocompression bonding as a means, and thereafter, the flexible printed wired board is configured in a multiple-folded form.

JP5399594B discloses an ultrasonic endoscope having an ultrasonic transmission/reception unit that transmits and receives ultrasonic waves; a wiring board electrically connected to a back side of the ultrasonic transmission/reception unit; a plurality of driver wires electrically connected to the wiring board; and a housing that houses the wiring board to hold the ultrasonic transmission/reception unit. The wiring board has a rigid circuit board electrically connected to a plurality of ultrasonic oscillators in the vicinity of central parts thereof in a width direction; and an enveloping part that wraps and bundles the driver wires, and is inserted into a housing in a state where the driver wires are wrapped and bundled by the enveloping part.

JP1996-004359A (JP-H08-004359A) discloses an ultrasound probe in which signal lines are alternately connected from both sides of an ultrasonic oscillator array disposed on a convex surface and electrodes are led out from one side surface side by a single flexible printed wired board having conductive paths formed on both surfaces thereof.

JP4980653B discloses an electronic scanning type ultrasound probe having respective pad electrodes of a pad electrode group that are arranged on an oscillator board of an ultrasonic oscillator unit so as to extend from the vicinity of a central part of the ultrasonic oscillator array in a width direction thereof and that are electrically connected to ultrasonic oscillators; and a coaxial cable assembly having a comb-like lead electrode group. Upon connection between the pad electrodes of the ultrasonic oscillator unit and leads of the coaxial cable assembly, alignment between the respective pad electrodes and the comb-like lead electrode group is performed.

JP3802756B discloses an ultrasound probe including a printed board having first and second signal pattern groups electrically connected to electrodes of an ultrasonic oscillator array in the vicinity of a central part of the ultrasonic oscillator array in a width direction thereof and electrically connected to halves of the electrodes of the ultrasonic oscillator array, respectively. The first and second signal pattern groups are wired with the coaxial cable in different directions, respectively.

SUMMARY OF THE INVENTION

Meanwhile, in the ultrasonic endoscopes disclosed in JP4445764B, JP5399594B, JP1996-004359A (JP-H08-004359A), JP4980653B, and JP3802756B, numerous ultrasonic oscillators are disposed in an array on the ultrasonic observation part provided at a distal end part, and cables are respectively wired to the ultrasonic oscillator. For example, the number of channels is as large as 48 to 192, the external diameter of ultrasonic observation part is small, and expensive, extremely fine cables are used as the cables. Therefore, in the current situation, wiring within the ultrasonic observation part is a complicated task, and numerous wiring lines are manually wired within a small distal end part. For this reason, the handling of the cables within the ultrasonic observation part with a small external diameter is complicated, and high filling is required. That is, since it is necessary to wire the cables in high density within the ultrasonic observation part in addition to the handling of the cables being complicated, this becomes a cause that the workability is poor and the manufacturing costs of the ultrasonic endoscope become high.

In spite of size reduction of the ultrasonic observation part being required in order to improve the workability and reduce the burden on the patient, as described above, there is a problem that the size reduction of the ultrasonic observation part is very difficult from viewpoints of the manufacture stability of the ultrasonic observation part, and the manufacturing costs thereof.

Additionally, in the techniques disclosed in JP4445764B and JP1996-004359A (JP-H08-004359A), a structure in which the flexible printed wired board of the ultrasonic oscillator unit is folded up multiple times is provided. Therefore, there is a problem that the wiring structure of the cable bundle and the flexible printed wired board is complicated. Even though the ultrasonic oscillator array, the cable bundle, and the flexible printed wired board are connected to each other by thermocompression bonding, there is still a problem in the workability of wiring. Particularly, in JP4445764B, there are problems that, during the manufacture of the ultrasonic oscillator unit, a burden is applied on a cable in a case where the flexible printed wired board is folded up multiple times, and the cable wiring line to which the burden is applied is disconnected.

Additionally, in any of the techniques disclosed in JP4445764B, JP5399594B, JP4980653B, and JP3802756B, the electrodes of the ultrasonic oscillator array and the wiring board are electrically connected to each other in the vicinity of the central part of the ultrasonic oscillator array in the width direction thereof. In this structure, there are problems that the manufacture is significantly difficult and the success rate of the manufacture is not high.

An object of the invention is to solve the above problems of the related arts and to provide an ultrasonic oscillator unit that can be small-sized, has excellent workability in a case where respective electrodes of an ultrasonic oscillator array and numerous cables are wired, has low difficulty of an operation step, has a wiring structure in which a load on a cable is unlikely to occur and there is less risk of disconnection, and that has a wiring structure suitable for use in an ultrasonic endoscope.

In order to achieve the above object, an ultrasonic oscillator unit comprises an ultrasonic oscillator array in which a plurality of ultrasonic oscillators having a rod shape are arranged in a circular-arc shape while aligning in a longitudinal direction of the rod shape; an electrode part that is provided on at least one end surface of the plurality of ultrasonic oscillators perpendicular to the longitudinal direction and has a plurality of electrodes electrically connected to the plurality of ultrasonic oscillators, respectively; a circular-arc backing material layer that is disposed on a rear surface of the ultrasonic oscillator array that becomes a center side of the circular-arc shape; and a cable wiring part including a flexible printed wired board in which a plurality of cables are disposed at a plurality of wiring lines electrically connected to the plurality of electrodes of the electrode part. The flexible printed wired board extends to a lower side of the backing material layer that becomes a side opposite to the ultrasonic oscillator array and is separated into a plurality of belt-like pieces in a comb shape. The cable wiring part has a cable connecting part including, in a comb shape, a plurality of strip-like electrode parts that are provided in the plurality of belt-like pieces. Each of the strip-like electrode parts is formed by linearly disposing at least one electrode pad in a longitudinal direction of each of the belt-like pieces on each belt-like piece.

Additionally, it is preferable that the ultrasonic oscillator unit further comprises a staircase part that is disposed to abut against a lower surface of the backing material layer, is perpendicular to a width direction of the backing material layer along the longitudinal direction of the rod shape, and becomes stepwise in the width direction of the backing material layer from an ultrasonic oscillator side at one end part of the ultrasonic oscillator array toward an ultrasonic oscillator side on the other end part thereof with respect to the lower surface of the backing material layer, a portion above the cable connecting part of the cable wiring part is disposed along the backing material layer, the plurality of belt-like pieces of the flexible printed wired board are bent along the lower surface of the backing material layer, are bent at respective steps of the staircase part again, and are disposed along the respective steps of the staircase part, and the plurality of strip-like electrode parts of the cable connecting part are respectively disposed on the belt-like pieces disposed along the respective steps of the staircase part.

Moreover, it is preferable that the cable connecting part has the same number of strip-like electrode parts as the number of the steps of the staircase part.

Additionally, it is preferable that a width of the plurality of strip-like electrode parts is narrower than a width, in a step difference direction, of the respective steps of the staircase part along which the strip-like electrode parts are respectively disposed.

Additionally, it is preferable that lengths of the respective strip-like electrode parts in a longitudinal direction thereof are longer as the strip-like electrode parts are disposed along lower steps of the staircase part, and the numbers of the electrode pads of the respective strip-like electrode parts are larger as the electrode pads are disposed along the lower steps of the staircase part.

Additionally, it is preferable that in the cable connecting part, the plurality of cables are wired so as to be directed from higher steps of the staircase part to lower steps thereof, using the electrode pads of each of the strip-like electrode parts as one end.

Additionally, it is preferable that the respective steps of the staircase part have a width wider than the strip-like electrode parts in the longitudinal direction of the strip-like electrode parts disposed along the steps and have wider width at lower steps.

Additionally, it is preferable that the staircase part is made of the same material as that of the backing material layer.

According to the invention, since the space for electrically connecting the ultrasonic oscillator array and the cables using the cable wiring part of a simple configuration can be efficiently used, the workability during wiring can be improved, the success rate in a case where the ultrasonic oscillator unit is manufactured can be improved, and the ultrasonic oscillator unit can be made small-sized.

DESCRIPTION OF THE PREFERRED EMBODIMENTS

An ultrasonic oscillator unit related to the invention will be described in detail with reference to a preferred embodiment illustrated in the attached drawings.

Figure 1:
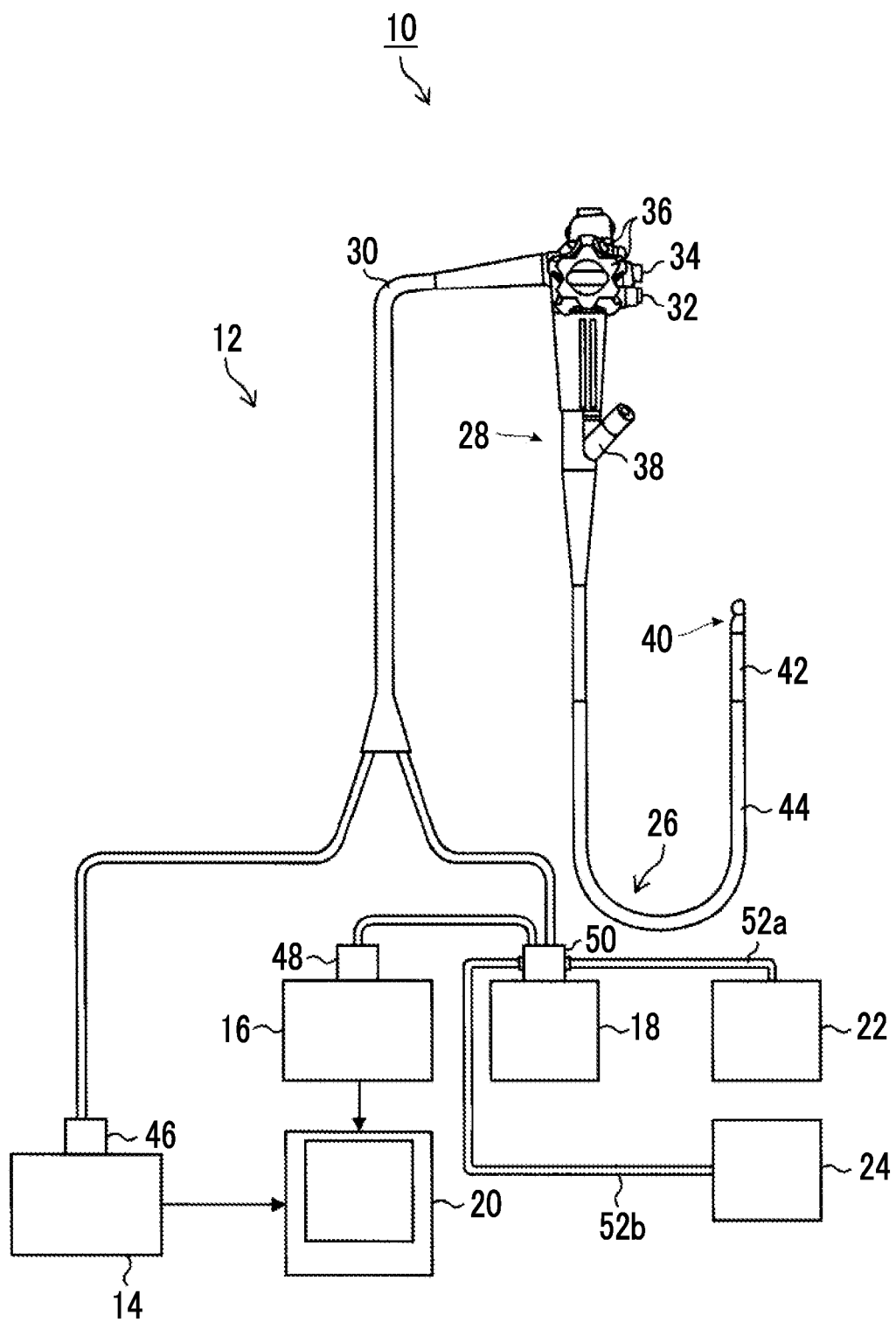
FIG. 1 is a schematic configuration view illustrating an example of the configuration of an ultrasonic inspection system using an ultrasonic endoscope to which an ultrasonic oscillator unit of the invention is applied.

FIG. 1 illustrates a schematic configuration view illustrating an example of the configuration of an ultrasonic inspection system using an ultrasonic endoscope to which an ultrasonic oscillator unit of the invention is applied.

The ultrasonic inspection system illustrated in FIG. 1 allows observation of the gallbladder or the spleen that is difficult in the ultrasonic inspection from the body surface of a subject, such as a patient, via alimentary canals, such as the esophagus, the stomach, the duodenum, the small intestine, and the large intestine that are body cavities of the subject, includes the ultrasonic oscillator unit of the invention, and acquires an ultrasound image of a region to be observed of the subject while inserting the ultrasonic endoscope having an ultrasonic observation part and an endoscope observation part into the body cavities of the subject to observe an endoscopic image of the subject. The ultrasonic observation part acquires an ultrasonic tomographic image (hereinafter referred to as the ultrasound image), and the endoscope observation part acquires an endoscopic optical image (hereinafter referred to as the endoscopic image).

As illustrated in FIG. 1, an ultrasonic inspection system 10 has an ultrasonic endoscope 12 that uses an ultrasonic oscillator unit 68 (refer to FIGS. 2 to 4) of the invention to be described below, an ultrasonic wave processor device 14 that creates an ultrasound image, an endoscope processor device 16 that creates an endoscopic image, a light source device 18 that supplies the illumination light for illuminating the inside of the body cavity of the subject to the ultrasonic endoscope 12 via a light guide (not illustrated), and a monitor 20 that displays the ultrasound image and the endoscopic image that are acquired from the ultrasonic wave processor device 14 and the endoscope processor device 16.

Moreover, the ultrasonic inspection system 10 further has a water supply pump with that is stored in the light source device 18 and that supplies water to the ultrasonic endoscope 12 (not illustrated), a water supply tank 22 that stores the water to be supplied to the ultrasonic endoscope 12 using the water supply pump, an air supply pump (not illustrated) that is stored in the light source device 18 for supplying air to the ultrasonic endoscope 12, and a suction pump 24 for suctioning an observation target from the endoscope distal end part 40 of the ultrasonic endoscope 12 to be described below. The ultrasonic wave processor device 14, the endoscope processor device 16, the light source device 18, the water supply tank 22, the suction pump 24, the water supply pump, and the air supply pump are connected to the ultrasonic endoscope 12, using a universal cord 30 (to be described below) of the ultrasonic endoscope 12.

The ultrasonic endoscope 12 of the ultrasonic inspection system 10 includes an insertion part 26 that has a distal end side inserted into the body cavity of the subject in order to observe targets, such as the gallbladder and the pancreas, and is inserted into the body cavity of the subject, which is disposed on a distal end side of the ultrasonic endoscope 12, an operating part 28 that is installed consecutively with a proximal end part of the insertion part 26 for allowing operators, such as a doctor and an engineer, to perform an operation, and the universal cord 30 that has one end connected to the operating part 28 and the other end connected to a plurality of devices for controlling the ultrasonic endoscope 12.

The ultrasonic wave processor device 14 of the ultrasonic inspection system 10 is a device for creating and supplying ultrasonic signals (data) for creating the ultrasonic waves in an ultrasonic oscillator array 100 (refer to FIGS. 2 to 4) of an ultrasonic oscillator unit 68 of an ultrasonic observation part 58 of an endoscope distal end part 40 of the insertion part 26 of the ultrasonic endoscope 12 to be described below. Additionally, the ultrasonic wave processor device 14 is a device for receiving and acquiring the echo signals (data), which is reflected from the region to be observed to which the ultrasonic waves are radiated, with the ultrasonic oscillator array 100, and for creating the ultrasound image that is obtained by performing various kinds of signal (data) processing on the acquired echo signals and is displayed on the monitor 20.

The endoscope processor device 16 of the of the ultrasonic inspection system 10 is a device for receiving and acquiring captured image signals (data) acquired from the region to be observed illuminated with the illumination light from the light source device 18 in the endoscope observation part 56 (refer to FIGS. 2 and 3) of the endoscope distal end part 40 of the insertion part 26 of the ultrasonic endoscope 12 to be described below and for creating the endoscopic image that is obtained by performing various kinds of signal (data) processing and image processing on the acquired image signals and is displayed on the monitor 20.

In addition, the processor devices 14 and 16 may be constituted of processors, such as a personal computer (PC).

In order to image the region to be observed within the body cavity to acquire the image signals with the endoscope observation part 56 (refer to FIGS. 2 and 3) of the ultrasonic endoscope 12 to be described below, the light source device 18 of the ultrasonic inspection system 10 is a device for generating Illumination light, such as white light consisting of three primary color lights, such as red light (R), green light (G), and blue light (B), or specific wavelength light to supply the Illumination light to the ultrasonic endoscope 12 to propagate the illumination light with a light guide or the like within the ultrasonic endoscope 12 (not illustrated), and emitting the illumination light from the endoscope observation part 56 of the endoscope distal end part 40 of the insertion part 26 of the ultrasonic endoscope 12 for illuminating the region to be observed within the body cavity with the illumination light.

The monitor 20 of the ultrasonic inspection system 10 receives respective video signals created by the ultrasonic wave processor device 14 and the endoscope processor device 16 to display the ultrasound image and the endoscopic image. The monitor 20 is capable of appropriately displaying only any one image of the ultrasound image and the endoscopic image through switching and simultaneously displaying both the images. In addition, a monitor for displaying the ultrasound image and a monitor for displaying the endoscopic image may be separately provided, or the ultrasound image and the endoscopic image may be displayed using any other forms.

The operating part 28 of the ultrasonic endoscope 12 has an air/water supply button 32 that is a switch for supplying air or supplying water to the endoscope distal end part 40 of the insertion part 26 to be described below, and a suction button 34 that is a switch that is disposed side by side with the air/water supply button 32 on the endoscope distal end part 40 side in a longitudinal direction of the ultrasonic endoscope 12 for suctioning the observation target while puncturing the observation target at a distal end of a puncturing needle of a treatment tool (not illustrated) delivered from the endoscope distal end part 40.

Moreover, the operating part 28 of the ultrasonic endoscope 12 has angle knobs 36 that are a pair of knobs each disposed on each side surface of the operating part 28 so as to sandwich the air/water supply button 32 and the suction button 34 and freely bend a bending part 42 (to be described below) vertically and horizontally by rotationally moving the respective knobs, and a treatment tool insertion port (forceps port) 38 that is disposed between the air/water supply button 32 and the insertion part 26 and allows treatment tools, such as forceps, a puncturing needle, and a high-frequency knife, which are delivered from the endoscope distal end part 40, to be inserted therethrough.

The insertion part 26 of the ultrasonic endoscope 12 has the endoscope distal end part (distal end rigid part) 40 that has ultrasonic oscillators 98 of the ultrasonic oscillator unit 68, an observation window 76 of an imaging unit 64, and the like (to be described below) and is formed of a rigid member, the bending part 42 that is installed consecutively with a proximal end side of the endoscope distal end part 40 and is freely bendable, and a flexible part 44 that couples a proximal end sides of the bending part 42 and a distal end side of the operating part 28 to each other, and is thin, elongated, rod-shaped, and flexible, sequentially from the distal end side.

The universal cord 30 of the ultrasonic endoscope 12 is a cord for connecting a plurality of devices for controlling the ultrasonic endoscope 12 and the ultrasonic endoscope 12 to each other, and is provided at a rear end of the ultrasonic endoscope 12. An ultrasonic wave connector 46 connected to the ultrasonic wave processor device 14, an endoscope connector 48 connected to the endoscope processor device 16, and a light source connector 50 connected to the light source device 18, the water supply tank 22, the suction pump 24, the water supply pump (not illustrated), and the air supply pump (not illustrated) are attachably and detachably connected to the other end part of the universal cord 30 with respect to a distal end part of the ultrasonic endoscope 12. Additionally, an air/water supply tube 52a having the other end connected to the water supply tank 22, and a suctioning tube 52b having the other end connected to the suction pump 24 are connected to the light source connector 50.

The air/water supply button 32 of the operating part 28 is a switch that controls the supply of air or water to the endoscope distal end part 40 of the insertion part 26, is connected the other end of a pipe line (not illustrated), which passes through the inside of the ultrasonic endoscope 12 and has one end leading to an air/water supply nozzle 62 of the endoscope observation part 56 of the endoscope distal end part 40 to be described above, and is connected to the other end of a pipe line (not illustrated) that has one end leading to the water supply tank 22 and the water supply pump (not illustrated) or the air supply pump (not illustrated). By pushing the air/water supply button 32, the water supply pump or the air supply pump, and the pipe lines communicating with the air/water supply nozzle 62 and the water supply tank 22 are connected to each other, and the water or air stored in the water supply tank 22 is supplied to the air/water supply nozzle 62. In addition, well-known methods, such as configuring the air/water supply button 32 with a two-step switching type, can be appropriately used as methods for switching connections of pipe lines of the water supply pump and the air supply pump.

The suction button 34 of the operating part 28 is a switch that controls the suction operation in the endoscope distal end part 40 of the insertion part 26, is connected the other end of a treatment tool insertion channel 61 (refer to FIG. 3) (to be described below) that passes through the inside of the ultrasonic endoscope 12 and has one end leading to the treatment tool delivery port 60 (refer to FIG. 3) of the endoscope distal end part 40, and is connected to the other end of a pipe line (not illustrated) that has one end leading to the suction pump 24. As for the suction button 34, by pushing the suction button 34 similarly to the above-described air/water supply button 32, the pipe lines leading to the treatment tool insertion channel 61 and the suction pump 24 are connected to each other, and suction is performed from the treatment tool delivery port 60. Additionally, in a case where a treatment tool (not illustrated) having a puncturing needle is inserted through the treatment tool insertion channel 61, suction of tissue of the observation target is performed from the distal end of the puncturing needle by pushing the suction button 34.

Figure 2:
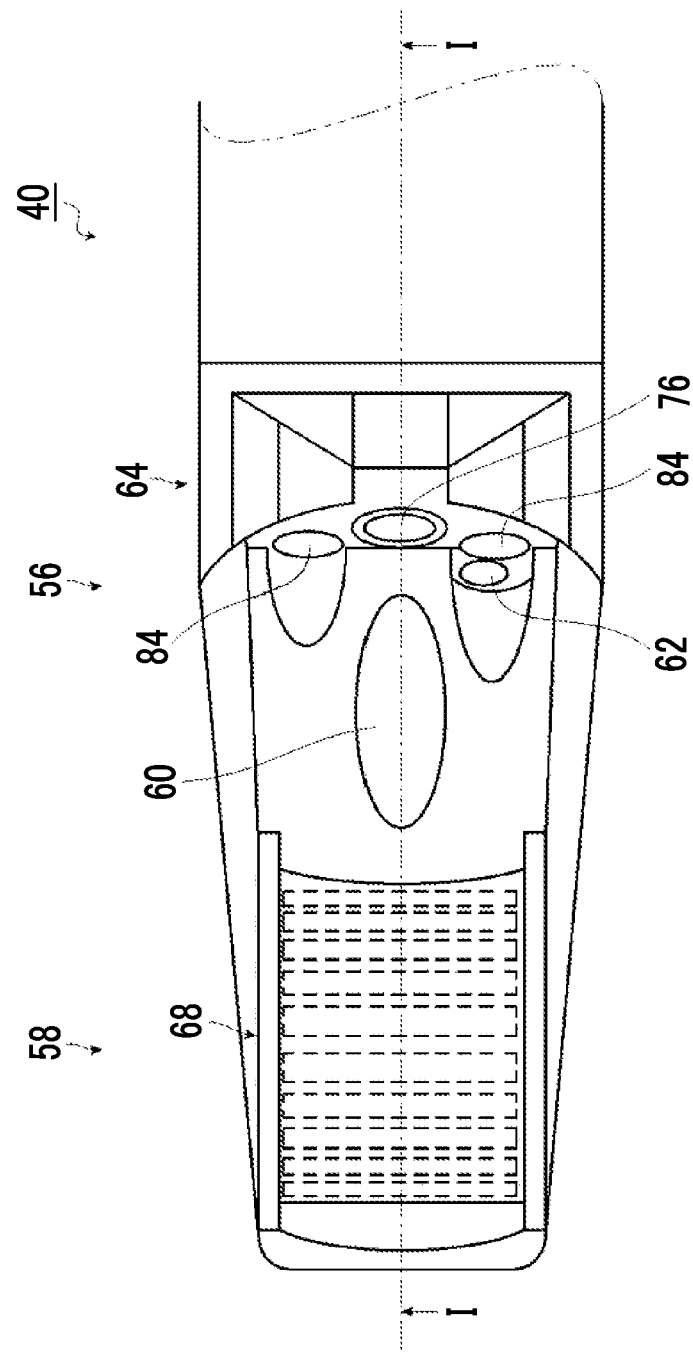
FIG. 2 is a partially enlarged plan view illustrating an endoscope distal end part of the ultrasonic endoscope illustrated in FIG. 1.
Figure 3:
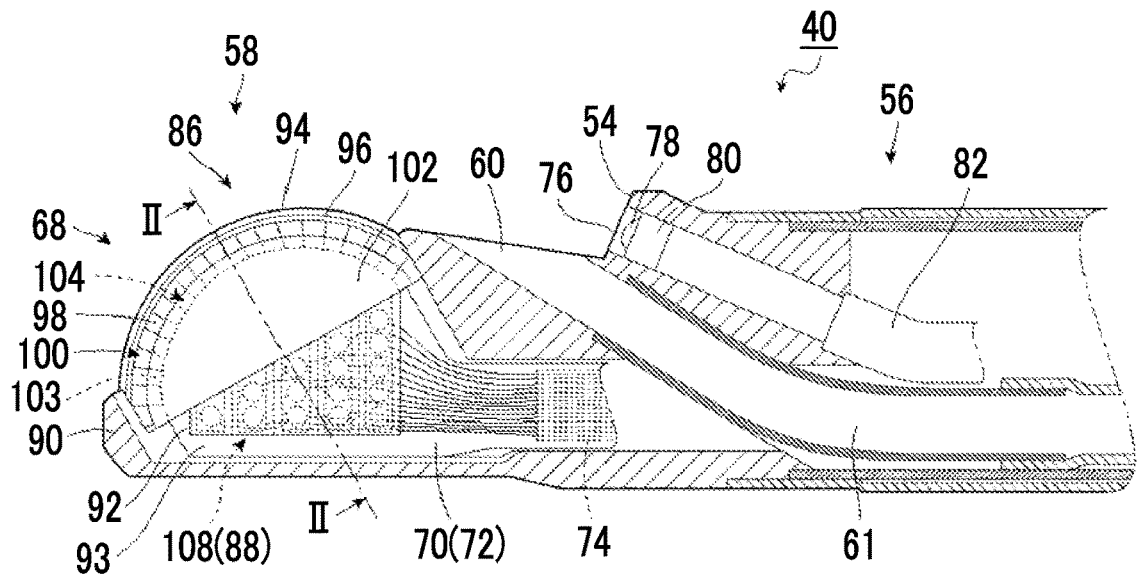
FIG. 3 is a view of the endoscope distal end part taken along line I-I illustrated in FIG. 2 and seen from an arrow direction and schematically illustrates a partially cross-sectional view of the endoscope distal end part of the ultrasonic endoscope illustrated in FIG. 2.

A partially enlarged plan view illustrating the endoscope distal end part of the ultrasonic endoscope illustrated in FIG. 1 is illustrated in FIG. 2. FIG. 3 is a view of the endoscope distal end part taken along line I-I illustrated in FIG. 2 and seen from an arrow direction and schematically illustrates a partially cross-sectional view of the endoscope distal end part of the ultrasonic endoscope illustrated in FIG. 2 cut with a centerline along a longitudinal direction thereof. As illustrated in FIGS. 2 and 3, the endoscope distal end part 40 of the insertion part 26 has an inclined surface part 54 formed on a proximal end side thereof, the inclined surface part 54 being an inclined surface having a large angle of elevation in a direction of a proximal end of the endoscope distal end part 40 with respect to a bottom surface of the endoscope distal end part 40, and has the endoscope observation part 56 that is provided on the inclined surface part 54 for acquiring the endoscopic image, the ultrasonic observation part 58 that is provided on the distal end side of the endoscope distal end part 40 for acquiring the ultrasound image, the treatment tool delivery port 60 that is provided between the endoscope observation part 56 and the ultrasonic observation part 58 and that delivers a treatment tool (not illustrated) within the body cavity of the subject, the treatment tool insertion channel 61 that allows the treatment tool insertion port 38 and the treatment tool delivery port 60 of the operating part 28 to communicate with each other for allowing the treatment tool to be inserted therethrough, and the air/water supply nozzle 62 that is provided between the endoscope observation part 56 and the treatment tool delivery port 60 for washing foreign matter or the like adhering to the endoscope observation part 56.

In addition, in the example illustrated in FIG. 2, although the treatment tool delivery port 60 is provided between the endoscope observation part 56 and the ultrasonic observation part 58, the invention is not particularly limited to the illustrated example. The treatment tool delivery port 60 may be provided within the endoscope observation part 56 or may be provided closer to the proximal end side (bending part 42 side) than the endoscope observation part 56. Additionally, a cable connecting part 108 of a cable wiring part 88 to be described below is illustrated in FIG. 3, as described above. However, FIG. 3 is a schematic view illustrated for description of the invention, and it is preferable that the total number of electrode pads 112 of cable connecting parts 108 disposed on both side surface sides of the backing material layer 102 in a width direction thereof is the same as the total number of the ultrasonic oscillators 98 that constitute the ultrasonic oscillator array 100.

The bending part 42 of the insertion part 26 illustrated in FIG. 1 is formed by coupling a plurality of bendable pieces to each other and is installed consecutively with the proximal end side of the endoscope distal end part 40. Additionally, the bending part 42 is freely bendable vertically and horizontally by the rotational movement of the pair of angle knobs 36 provided at the operating part 28. In this way, since the bending part 42 is remotely and freely bending-operated by using the angle knobs 36 as operating means, the endoscope distal end part 40 can be directed to a direction desired to an operator.

Since the flexible part 44 of the insertion part 26 couples a proximal end side of the bending part 42 and the distal end side of the operating part 28 to each other, and is thin, elongated, rod-shaped, and flexible, even in a case where the flexible part 44 is within the body cavity of the subject having a complicated structure, the flexible part 44 can be inserted so as to follow the bending-operated bending part 42.

The endoscope observation part 56 of the endoscope distal end part 40 illustrated in FIG. 2 has the imaging unit 64 that is provided so as to pass through the inside of the ultrasonic endoscope 12 from the center of the inclined surface part 54 and captures the endoscopic image, and an illumination unit 66 that is disposed side by side with the imaging unit 64 for illuminating a region to be observed using the illumination light from the light source device 18.

As illustrated in FIG. 3, the ultrasonic observation part 58 of the endoscope distal end part 40 to be inserted into the inside of the body of the subject in order to observe targets, such as the gallbladder and the pancreas has a cable dispersion part 72 including a plurality of cables 70 electrically connecting the ultrasonic oscillator unit 68, which transmits and receives the ultrasonic signals with respect to the observation target, to the universal cord 30 that transmit driving signals of the ultrasonic waves to the ultrasonic oscillator unit 68, the universal cord 30 being connected to the ultrasonic wave processor device 14 that analyzes signals of the reflected waves from the observation target that are received from the ultrasonic oscillator unit 68, and creates the ultrasound image, and a cable covering part 74 that binds the cable dispersion part 72.

The treatment tool delivery port 60 of the endoscope distal end part 40 illustrated in FIG. 3 is provided on a distal end side of the imaging unit 64, and a treatment tool (not illustrated), which is inserted from the treatment tool insertion port 38 of the operating part 28 and passes through the treatment tool insertion channel 61, is delivered from the treatment tool delivery port 60. In addition, in FIG. 2, although the treatment tool delivery port 60 is located between the endoscope observation part 56 and the ultrasonic observation part 58, it is preferable to dispose the treatment tool delivery port 60 close to the ultrasonic observation part 58 in a case where the movement of the treatment tool introduced into the body cavity from the treatment tool delivery port 60 is confirmed with the ultrasound image.

Additionally, although not illustrated, a rising stand that changes a delivery direction of the treatment tool introduced into the body cavity from the treatment tool delivery port 60 may be provided inside the treatment tool delivery port 60. A wire (not illustrated) is attached to the rising stand, the standing angle of the rising stand is changed by a push/pull operation resulting from the operation of, for example, a standing lever (not illustrated) provided in the operating part 28, and thereby the treatment tool is delivered in a desired direction.

The air/water supply nozzle 62 of the endoscope distal end part 40 illustrated in FIG. 2 is a nozzle that is provided between the imaging unit 64 and the treatment tool delivery port 60 for washing the observation window 76 of the imaging unit 64 to be described below. By pushing the air/water supply button 32 of the operating part 28, air or water is supplied from the air supply pump (not illustrated) or the water supply pump (not illustrated) through a flow channel (not illustrated) for air supply or water supply provided within the ultrasonic endoscope 12 to the air/water supply nozzle 62.

Additionally, the cable dispersion part 72 of the endoscope distal end part 40 illustrated in FIG. 3 includes the plurality of cables 70 electrically connected to the ultrasonic oscillator unit 68, and is a portion in which the plurality of cables 70 are not bound in the cable covering part 74. The cable dispersion part 72 is fixed using electrical connection means, such as soldering or conductive paste in a wiring portion between the ultrasonic oscillator unit 68 and the cables 70 constituting the cable dispersion part 72.

The imaging unit 64 of the endoscope observation part 56 illustrated in FIG. 3 has a transparent observation window 76 disposed at the inclined surface part 54 for protecting an imaging optical system disposed at the rear thereof, an objective lens 78 of an observation optical system that is disposed behind the observation window 76 and inside the endoscope distal end part 40, an imaging element 80, such as a charge coupled device (CCD) or a complementary metal-oxide semiconductor (CMOS) that is disposed at a focusing position of the objective lens 78 inside the endoscope distal end part 40, and a signal cable 82 electrically connected to the imaging element 80, and the universal cord 30 connected to the light source device 18 through a pipe line (not illustrated) inside the ultrasonic endoscope 12.

The illumination unit 66 of the endoscope observation part 56 has a pair of transparent illumination windows 84 that are provided side by side at the imaging unit 64, are provided side by side on both sides of the observation window 76 in the inclined surface part 54 and protect an illumination optical system disposed at rear thereof, and the light guide (not illustrated) that is disposed behind the illumination windows 84 and inside the endoscope distal end part 40 for transmitting the illumination light from the light source device 18 to the illumination windows 84.

The observation window 76 of the imaging unit 64 is disposed at the inclined surface part 54, and the image light of the observation target incident from the observation window 76 is focused on an imaging surface of the imaging element 80 by the objective lens 78. The imaging element 80 photoelectrically converts the image light of the observation target transmitted through the observation window 76 and the objective lens 78 and focused on the imaging surface of the imaging element 80 and outputs imaging signals to the endoscope processor device 16. The imaging signals output from the imaging element 80 are transmitted to an endoscope processor device 16 via a signal cable 82 and the universal cord 30. The endoscope processor device 16 performs signal processing and image processing on the imaging signals transmitted in this way, creates an endoscope optical image, and displays the endoscopic image on the monitor 20.

The illumination windows 84 of the illumination unit 66 are a pair of windows that are provided side by side on both sides of the observation window 76 of the imaging unit 64, and an exit end of the light guide (not illustrated), which guides the illumination light from the light source device 18, to the observation window 76, is connected to the illumination windows 84. The light guide extends from the illumination windows 84 to the light source device 18 through the inside of the ultrasonic endoscope 12, and an incident end of the light guide is stored within the light source device 18. The Illumination light emitted by the light source device 18 is propagated to the light guide and is radiated from the illumination windows 84 to the observation target.

Figure 4:
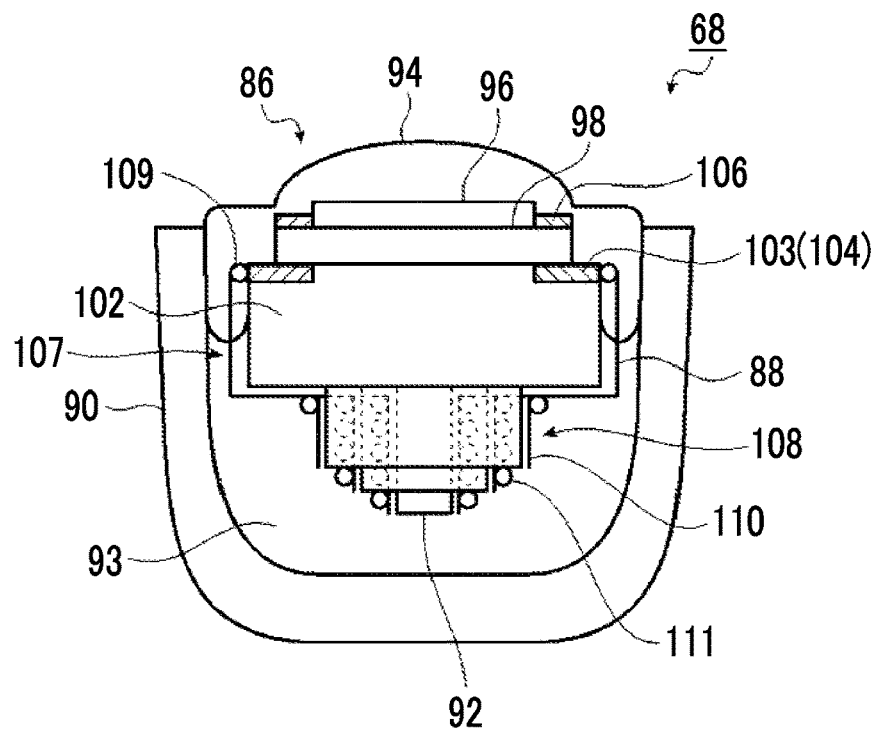
FIG. 4 is a view of the endoscope distal end part taken along line II-II illustrated in FIG. 3 and seen from an arrow direction and is a cross-sectional view of an example of an ultrasonic observation part of the endoscope distal end part of the ultrasonic endoscope illustrated in FIG. 3.

FIG. 4 is a view of the endoscope distal end part taken along line II-II illustrated in FIG. 3 and seen from an arrow direction and is a cross-sectional view of an example of the ultrasonic observation part of the distal end part of the ultrasonic endoscope illustrated in FIG. 3.

The ultrasonic oscillator unit 68 of the ultrasonic observation part 58 illustrated FIGS. 3 and 4 has a laminated body 86 that is disposed at a distal end portion of the ultrasonic observation part 58, transmits and receives the ultrasonic waves, and has a laminated structure, the cable wiring part 88 that are electrically connected to the laminated body 86 and the cable dispersion part 72 including the plurality of cables 70, a housing 90 that is provided in order to protect a wiring portion between the laminated body 86 and the plurality of cables 70 from the outside of the ultrasonic observation part 58, and surrounds side surfaces and lower surface excluding an upper surface of the laminated body 86 and the cable wiring part 88 in a case where a surface of the laminated body 86 that transmits and receives the ultrasonic waves is defined as the upper surface, a staircase part 92 that is disposed to abut against a bottom surface of the laminated body 86 on the housing 90 side and has a staircase shape for allowing a lower end side of the cable wiring part 88 to extend along them, and a filler layer 93 for filling a gap between the laminated body 86, the housing 90, and the staircase part 92 in order to fix the wiring portion of the cable wiring part 88.

In addition, since FIG. 4 is a schematic view illustrated for description of the invention and does not illustrate the details similarly to FIG. 3, it is needless to say that the arrangement locations, sizes, and shapes of the respective members illustrated in FIG. 4 may be appropriately changed without departing from the scope of the invention.

The laminated body 86 of the ultrasonic oscillator unit 68 has a laminated structure, and has an acoustic lens 94 that is located at an uppermost part in a case where a surface that transmits and receives the ultrasonic waves is defined as an upper surface for converging the ultrasonic waves output from the ultrasonic oscillator array 100 to be described below and the ultrasonic waves reflected from the observation target, an acoustic matching layer 96 that is located under the acoustic lens 94 for matching the acoustic impedance of the ultrasonic oscillators 98 constituting the ultrasonic oscillator array 100 with the acoustic impedance of the observation target, the ultrasonic oscillator array 100 which is located under the acoustic matching layer 96 and in which the plurality of rod-shaped ultrasonic oscillators 98 that transmit and receive the ultrasonic waves are arranged in a longitudinal direction of the rod shape are aligned in a circular-arc array, and a backing material layer 102 that is located on a rear surface becoming a circular-arc center side of the ultrasonic oscillator array 100 for mechanically supporting the ultrasonic oscillator array 100 and damping the ultrasonic waves propagated to a lower side of the ultrasonic oscillator array 100.

As illustrated in FIGS. 3 and 4, the acoustic matching layer 96 and the ultrasonic oscillator array 100 are disposed in a semicylindrical shape, and the acoustic lens 94 is disposed along the acoustic matching layer 96 disposed in the semicylindrical shape. Additionally, in the cross-sectional view illustrated in FIG. 3, the backing material layer 102 has a semicircular columnar shape. However, the backing material layer 102 may be disposed so as to abut against the entire lower surface of the ultrasonic oscillator array 100, and the shape of a lower surface of the backing material layer 102 is not particularly limited.

The cable wiring part 88 of the ultrasonic oscillator unit 68 is configured using a flexible printed wired board. The cable wiring part 88 is electrically connected to the plurality of cables 70 constituting the cable dispersion part 72, and an electrode part 104 of the ultrasonic oscillator array 100 to be described below. The cable wiring part 88 is disposed to extend to a lower side of the backing material layer 102 that becomes a side opposite to the ultrasonic oscillator array 100. The cable wiring part 88 includes an oscillator connecting part 107 and the cable connecting part 108. Here, the oscillator connecting part 107 is a portion disposed along the backing material layer 102 of the laminated body 86 electrically connected to the electrode part 104 of the ultrasonic oscillator array 100. Additionally, the cable connecting part 108 is disposed along the staircase part 92 and is electrically connected to the plurality of cables 70 of the cable dispersion part 72.

Figure 5:
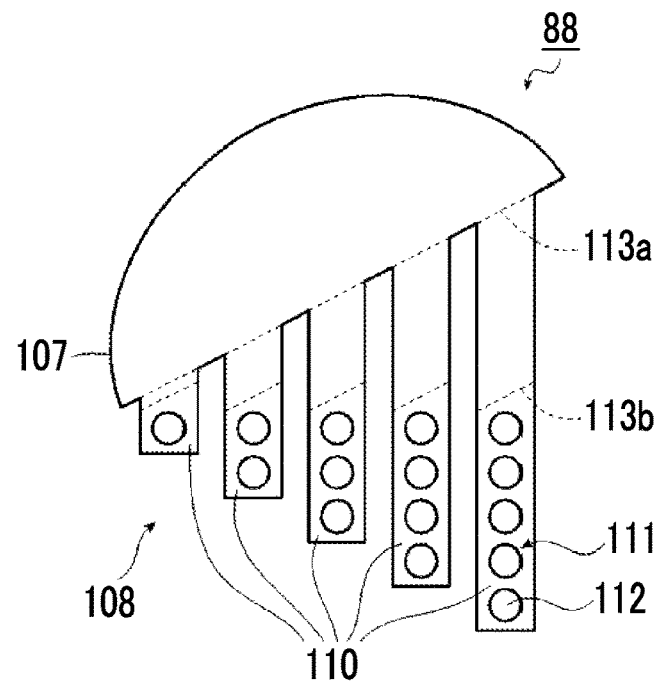
FIG. 5 is a schematic view illustrating the configuration of a cable wiring part of the invention.
Figure 6:
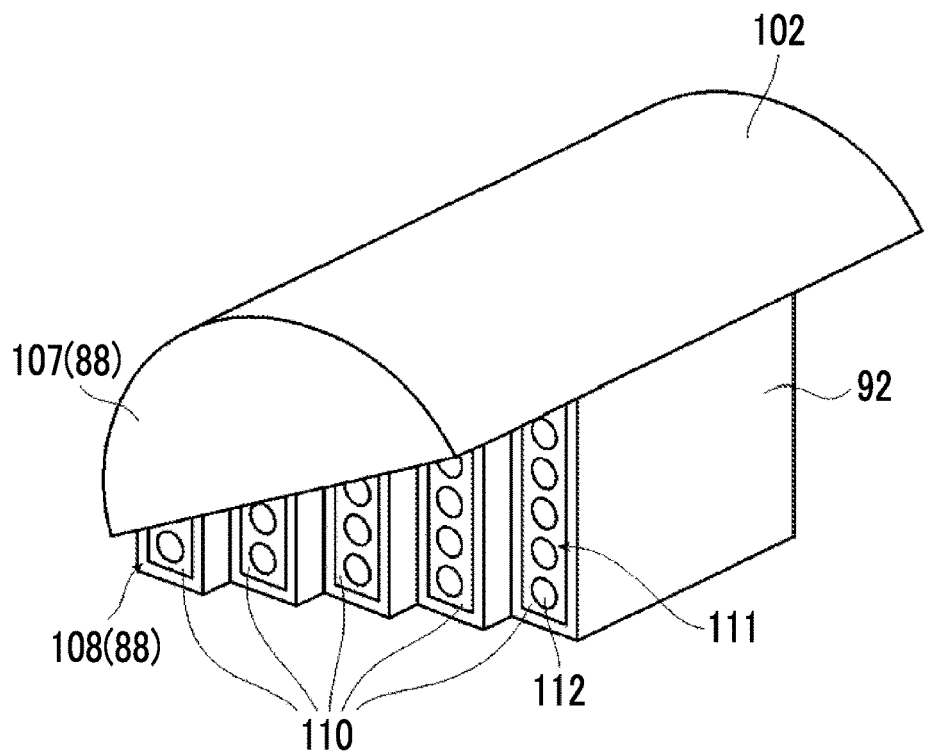
FIG. 6 is a perspective view illustrating a state where a laminated body and a staircase part that are illustrated in FIG. 3, and the cable wiring part illustrated in FIG. 5 are assembled together.

Moreover, as illustrated in FIGS. 5 and 6, the cable wiring part 88 of the ultrasonic oscillator unit 68 is separated into a plurality of belt-like pieces 110 in a comb shape in a portion extending to the lower side of the backing material layer 102 that becomes the side opposite to the ultrasonic oscillator array 100. The cable connecting part 108 of the cable wiring part 88 is the portion separated into the plurality of belt-like pieces 110 in a comb shape, and includes a plurality of strip-like electrode parts 111 provided at the plurality of belt-like pieces 110, respectively, in a comb shape. Moreover, as illustrated in FIG. 6, the cable wiring part 88 is disposed along each side surface, in the width direction, of the backing material layer 102 of the laminated body 86, and the staircase part 92.

In addition, FIGS. 5 and 6 are schematic views illustrated for description of the invention, and it is preferable that the total number of the electrode pads 112 of cable connecting parts 108 disposed on both side surface sides of the backing material layer 102 in the width direction thereof is the same as the total number of the ultrasonic oscillators 98 that constitute the ultrasonic oscillator array 100. Additionally, FIG. 6 is a view illustrating only the backing material layer 102, each cable wiring part 88, and the staircase part 92 in the laminated body 86 except for the acoustic lens 94, the acoustic matching layer 96, and the ultrasonic oscillator array 100 for description of the invention. For that reason, in a case where the ultrasonic oscillator unit 68 of the invention is disposed in the ultrasonic observation part 58, it is preferable that the cable wiring part 88 and the staircase part 92 are respectively disposed in the laminated body 86.

The housing 90 of the ultrasonic oscillator unit 68 illustrated in FIGS. 3 and 4 is made of a rigid member, such as rigid resin, and protects the side surfaces and the lower surface of the laminated body 86 and the cable wiring part 88 from the outside. The housing 90 abut against the side surfaces of the acoustic lens 94 of the laminated body 86 (to be described below) and the side surfaces of the laminated body 86 in the width direction thereof, and surrounds the side surfaces and a lower part of the laminated body 86 in the width direction thereof and the cable wiring part 88.

The filler layer 93 of the ultrasonic oscillator unit 68 is provided so as to fill the gap between the laminated body 86, the housing 90, and the staircase part 92. The filler layer 93 fixes a wiring portion between the cable wiring part 88 and the cables 70 to prevent disconnection of the portion. Additionally, the filler layer 93 also plays a role of fixing the positions of the laminated body 86 and the staircase part 92 disposed at the endoscope distal end part 40.

Moreover, it is preferable that the acoustic impedances of the filler layer 93 of the ultrasonic oscillator unit 68 and the backing material layer 102 are matched with each other such that the ultrasonic waves, which are oscillated from the ultrasonic oscillator array 100 of the laminated body 86 and propagated to a lower side thereof, are not reflected at a boundary between the filler layer 93 and the backing material layer 102 and such that the ultrasonic waves oscillated from the ultrasonic oscillator array 100 are reflected in the observation target or its peripheral part and sufficiently damp the ultrasonic waves propagated to the lower side of the ultrasonic oscillator array 100. For that reason, in a case where the acoustic impedance of the filler layer 93 is defined as Zp and the acoustic impedance of the backing material layer 102 is defined as Zb, it is preferable that an acoustic impedance reflectivity Q of the filler layer 93 and the backing material layer 102 expressed by the following Equation (1) is 50% or less.

$$Q=100\times|Zp-Zb|/(Zp+Zb) \qquad (1)$$

Here, the unit of the acoustic impedance Zp and Zb is $kg/m^2 s$. In addition, kg represents kilogram, m represents meter and s represents second.

Additionally, in order for the acoustic impedance reflectivity Q of the filler layer 93 and the backing material layer 102 to be 50% or less, for example, a filler of the same material as the backing material layer 102 may be used for the material of the filler layer 93. In a case where hard rubber or the like to which an ultrasonic damping material, such as ferrite or ceramics, is added as the material of the backing material layer 102 is used, epoxy resin to which a heat conduction member, such as ceramics, is added may be used as the filler layer 93.

The above acoustic impedance reflectivity is an index showing the easiness of reflection of the ultrasonic waves (acoustic beams) on a boundary surface between the filler layer 93 and the backing material layer 102, that is, shows that the acoustic impedance of the filler layer 93 and the acoustic impedance of the backing material layer 102 are matched with each other as the value thereof is closer to 0%. In a case where the above acoustic impedance reflectivity is about 50% or less, the noise caused by the ultrasonic waves propagated to the lower side of the ultrasonic oscillator array 100 can be processed to such a degree that no hindrance is caused in the creation of the ultrasound image in the ultrasonic wave processor device 14 using the ultrasonic signals received in the ultrasonic oscillator array 100.

Additionally, in a case where the ultrasonic waves are oscillated from the ultrasonic oscillator array 100 of laminated body 86 of the ultrasonic oscillator unit 68, the driving signals transmitted from the ultrasonic wave processor device 14 to the ultrasonic oscillator array 100 become thermal energy and the ultrasonic oscillator array 100 generates heat. Therefore, it is preferable that the filler layer 93 has heat dissipation. For that reason, it is preferable that the thermal conductivity of the filler layer 93 is more than 1.0 W/(m·K), for example, the epoxy resin with to which the heat conduction member, such as ceramics, is added may be used as the filler layer 93. Here, W represents watt, m represents meter and K represents Kelvin.

As illustrated in FIGS. 3, 4, and 6, the staircase part 92 of the ultrasonic oscillator unit 68 that is one of the features of the invention is disposed to abut against the lower surface of the backing material layer 102 opposite to the ultrasonic oscillator array 100 of the laminated body 86, is orthogonal to the width direction of the backing material layer 102 along the longitudinal direction of the rod shape of the ultrasonic oscillators 98, has a staircase shape that becomes stepwise in the width direction of the backing material layer 102 from the ultrasonic oscillators 98 side at one end part, in a radial direction, of the ultrasonic oscillator array 100 toward the ultrasonic oscillators 98 side at the other end part with respect to the lower surface of the backing material layer 102. Additionally, respective steps of the staircase part 92 become longer in a longitudinal direction as the steps become thin in the width direction of the backing material layer 102 (the steps are lower). In addition, in order to enhance the workability of wiring between the plurality of cables 70 of the cable dispersion part 72 and the respective electrode pads 112 of the strip-like electrode parts 111 and in order to enhance the durability of the wiring portion, it is preferable that the respective steps of the staircase part 92 are longer in the longitudinal direction than the respective strip-like electrode parts 111 disposed along the respective steps as will be described below.

In addition, the material used for the staircase part 92 are not particularly limited as long as the material maintains a staircase shape and do not cause hindrance in signals used for ultrasonic observation. For that reason, although one obtained by machining a well-known base can be used as the staircase part 92, the same material as the backing material layer 102 can also be used such that an acoustic impedance difference is not caused between the staircase part 92 and the backing material layer 102 of the laminated body 86.

Additionally, as illustrated in FIG. 3, in the staircase part 92 of the ultrasonic oscillator unit 68, it is preferable that the cable connecting part 108 of the cable wiring part 88 disposed along the staircase part 92 and the plurality of cables 70 of the cable dispersion part 72 are disposed so that the plurality of cables 70 can be efficiently wired such that the cables come into contact with each other. For that reason, in a case where the ultrasonic oscillator unit 68 is disposed at the ultrasonic observation part 58 of the endoscope distal end part 40, it is preferable that a direction in which the steps of the staircase part 92 become lower is orientated in a direction in which the cable dispersion part 72 is located. For that reason, the staircase part 92 is disposed to abut against the lower surface of the backing material layer 102 such that the longitudinal direction of each of the steps become oblique with respect to the lower surface of the backing material layer 102 of the laminated body 86. In addition, the staircase part 92 may be disposed to abut against the backing material layer 102 and may be bonded to the lower surface of the backing material layer 102, using a well-known adhesive or the like.

The oscillator connecting part 107 of the cable wiring part 88 illustrated in FIGS. 4 and 5 is a member that is provided on an upper side of the cable connecting part 108 and is disposed along each side surface, in the width direction, of the backing material layer 102 of the laminated body 86. As illustrated in FIG. 4, the oscillator connecting part 107 has a plurality of oscillator connecting terminals 109 that are terminals electrically connected to the electrode part 104 of the ultrasonic oscillator array 100, using the means, such as wire bonding and conductive paste, on each side surface of the backing material layer 102 in the width direction thereof. Additionally, a first bent part 113a for allowing the cable wiring part 88 to be bent on the staircase part 92 side is provided at lower end of each side surface of the backing material layer 102 in the width direction thereof at a lower end of the oscillator connecting part 107. In addition, the oscillator connecting terminals 109 of the oscillator connecting part 107 may be electrically connected to the electrode part 104 of the ultrasonic oscillator array 100 using simple means, and may be provided on the surface of the oscillator connecting part 107 opposite to the backing material layer 102. Moreover, a position where the electrode part 104 and the oscillator connecting terminals 109 are electrically connected to each other may be appropriately changed n accordance with the shape of the endoscope distal end part 40, the shape of the laminated body 86, and the like. That is, the electrode part 104 and the oscillator connecting terminals 109 may be electrically connected to each other on each side surface of the backing material layer 102 in the width direction thereof, or may be electrically connected to each other on an upper surface of the backing material layer 102.

As illustrated in FIG. 5, the cable connecting part 108 of the cable wiring part 88 that is another feature of the invention is the portion of the cable wiring part 88 opposite to the oscillator connecting part 107 wired to the electrode part 104 of the ultrasonic oscillator array 100, and are wired to the plurality of cables 70 of the cable dispersion part 72. Moreover, the cable connecting part 108 is separated into the plurality of belt-like pieces 110, and includes a plurality of strip-like electrode parts 111, which are respectively provided at the plurality of belt-like pieces 110 and include at least one electrode pad 112, in a comb shape. The cable connecting part 108 is disposed along a bottom surface of the backing material layer 102, and the steps of the staircase part 92, as illustrated in FIGS. 4 and 6, in order to dispose the strip-like electrode parts 111 side by side in a stepwise fashion.

Additionally, as illustrated in FIGS. 4 and 6, the cable connecting part 108 of the cable wiring part 88 is disposed along the respective steps of the staircase part 92. Thus, it is preferable to have the same number of strip-like electrode parts 111 as the number of steps of the staircase part 92 from viewpoints of improving the workability in wiring to the cables 70 of the cable dispersion part 72, keeping the cables 70 wired to the strip-like electrode parts 111 of the cable connecting part 108 from coming into contact with each other, and the like. For that reason, it is preferable that the plurality of strip-like electrode parts 111 are respectively disposed along the respective steps of the staircase part 92 having corresponding lengths in the longitudinal direction thereof. Moreover, from the same reasons as above, such as the workability of wiring and the contact between the cables 70, it is preferable to dispose the respective strip-like electrode parts 111 along the respective steps of the staircase part 92 so as not to project out of the respective steps of the staircase part 92. For that reason, it is preferable that the width of the plurality of strip-like electrode parts 111 are respectively narrower than the width, in a step difference direction, of the respective steps of the staircase part 92 and are respectively shorter than the length, in the longitudinal direction, of the respective steps of the staircase part 92. In addition, for example, a well-known adhesive or the like may be used as means for disposing the strip-like electrode parts 111 along the staircase part 92.

The strip-like electrode parts 111 of the cable connecting part 108 are electrode parts in which at least one electrode pad 112 is linearly provided in the longitudinal direction of the plurality of strip-shaped belt-like pieces 110 that are provided such that the cable connecting part 108 is comb-like, and are respectively disposed along the respective steps of the staircase part 92. That is, the strip-like electrode parts 111 are disposed on the plurality of belt-like pieces 110 that are bent along the lower surface of the backing material layer 102, are bent again at the respective steps of the staircase part 92, and are provided with the cable wiring part 88 disposed along the respective steps of the staircase part 92. For that reason, each strip-like electrode part 111 is formed such that the longitudinal direction thereof extends obliquely with respect to the first bent part 113a that is a boundary between the oscillator connecting part 107 and the cable connecting part 108. The first bent part 113a is a portion that that is formed by each belt-like piece 110 of the cable wiring part 88 being bent along the lower surface of the backing material layer 102.

Moreover, the strip-like electrode part 111 has a second bent portion 113b for being bent again at a boundary line between the backing material layer 102 of the laminated body 86 and the staircase part 92 in the middle thereof, and has at least one or more electrode pads 112 that are aligned linearly in the longitudinal direction of the strip-like electrode part 111 below the second bent portion 113b. That is, the portion sandwiched between the first bent part 113a and the second bent portion 113b is a portion along the bottom surface of the backing material layer 102, and the portion below the second bent portion 113b is a portion along each step of the staircase part 92.

Additionally, the strip-like electrode parts 111 of the cable connecting part 108 are longer in their length in the longitudinal direction and have more electrodes as the strip-like electrode parts 111 are disposed along lower steps of the staircase part 92. For that reason, as illustrated in FIG. 3, in a case where the ultrasonic oscillator unit 68 is disposed in the endoscope distal end part 40, access to the respective electrode pads 112 of the plurality of strip-like electrode parts 111 disposed along the staircase part 92 from the cable dispersion part 72 located closer to a proximal end side of the endoscope distal end part 40 than the staircase part 92 becomes easy. In this way, according to the above-described staircase part 92 and cable connecting part 108, the plurality of strip-like electrode parts 111 and cables 70 can be wired while effectively using the space within the endoscope distal end part 40 such that the plurality of cables 70 do not come into contact with each other, and workability can be also improved in wiring task.

The acoustic lens 94 of the laminated body 86 illustrated in FIG. 4 is a lens for converging the ultrasonic waves, and Is disposed so as to abut against the upper surfaces or side surfaces of the acoustic matching layer 96, the ultrasonic oscillator array 100, and the backing material layer 102, respectively, and cover the middle of each side surface of the backing material layer 102 in the width direction, in order to protect the acoustic matching layer 96, the ultrasonic oscillator array 100, and the backing material layer 102 that are laminated under the acoustic lens 94. Additionally, the acoustic lens 94 has a convex shape such that the acoustic lens 94 covers an upper part of the ultrasonic oscillator array 100 in the width direction of the laminated body 86 in order to converge the ultrasonic waves oscillated from the ultrasonic oscillator array 100 toward the observation target or in order to converge the ultrasonic waves reflected from the observation target toward the ultrasonic oscillator array 100. In addition, the acoustic lens 94 is disposed at the above-described position after the wiring task of the electrode part 104 and the upper electrode part 106 of the ultrasonic oscillator array 100 to be described below is completed. Additionally, the acoustic lens 94 is made of, for example, silicon-based resin, such as millable type silicone rubber or liquid silicone rubber, butadiene-based resin, polyurethane-based resin, or the like. Moreover, in order to match the acoustic impedance of the subject that is the observation target for ultrasonic observation with the acoustic impedance of the ultrasonic oscillators 98 that constitutes the ultrasonic oscillator array 100 and increase the transmittance of the ultrasonic waves to the subject, powder, such as titanium oxide, alumina, or silica, is mixed with the acoustic lens 94 as needed.

The acoustic matching layer 96 of the laminated body 86 is a layer for matching the acoustic impedances of the ultrasonic oscillator array 100 and the observation target, which are made of epoxy resin or the like, with each other. Since the acoustic matching layer 96 is installed such that a lower surface of the acoustic matching layer 96 is installed so as to abut against an upper surface of the ultrasonic oscillator array 100, but has a width shorter than the ultrasonic oscillator array 100 in the width direction of the laminated body 86, the acoustic matching layer 96 partially covers the upper surface of the ultrasonic oscillator array 100 such that both end parts or any one end part of the ultrasonic oscillator array 100 in the width direction thereof is removed. For that reason, the ultrasonic waves contributing to the observation of the target among the ultrasonic waves transmitted from the ultrasonic oscillator array 100 are only the ultrasonic waves that have passed through the acoustic matching layer 96, that is, only the ultrasonic waves transmitted from the ultrasonic oscillator array 100 in a region inside the side surfaces of the acoustic matching layer 96 in the width direction thereof.

The ultrasonic oscillator array 100 of the laminated body 86 is an array in which the plurality of ultrasonic oscillators 98 having a rod shape are aligned in the longitudinal direction of the rod shape and arranged in a circular-arc shape. The plurality of ultrasonic oscillators 98 is, for example, 48 to 192 ultrasonic oscillators 98 having a rod shape, such as a rectangular parallelepiped shape, and therefore, the ultrasonic oscillator array 100 is an array of 48 to 192 channels.

That is, the ultrasonic oscillator array 100 is an array in which the plurality of ultrasonic oscillators 98 are arranged at a specified pitch in a one-dimensional array as in the example illustrated in FIG. 3 as an example. In this way, the ultrasonic oscillators 98 that constitute the ultrasonic oscillator array 100 are arranged at equal intervals in a convexly curved shape in an axis direction (the longitudinal axis direction of the insertion part 26) of the endoscope distal end part 40 and are sequentially driven on the basis of driving signals input from the ultrasonic wave processor device 14. Accordingly, convex electronic scanning is performed using a range where the ultrasonic oscillators 98 illustrated in FIG. 2 are arranged, as a scanning range.

As illustrated in FIG. 4, the ultrasonic oscillator array 100 of the laminated body 86 is an array that transmits the ultrasonic signals to the observation target and receives the ultrasonic waves reflected from the observation target to convert the received ultrasonic waves into electrical signals, and is disposed such that a rear surface that becomes a circular-arc center side of the ultrasonic oscillator array 100 abuts against the upper surface of the backing material layer 102.

Additionally, the ultrasonic oscillator array 100 has the electrode part 104 that is provided at least on one surface perpendicular to the longitudinal direction of the plurality of ultrasonic oscillators 98 constituting the ultrasonic oscillator array 100 and that includes a plurality of oscillator electrodes 103 electrically connected to the plurality of ultrasonic oscillators 98, respectively. Each of the oscillator electrodes 103 of the electrode part 104 is electrically connected to each of a plurality of the cable wiring parts 88 in addition to each of the plurality of ultrasonic oscillators 98. Additionally, an upper electrode part 106, which is electrically connected to the plurality of ultrasonic oscillators 98 constituting the ultrasonic oscillator array 100 and a grounding electrode (not illustrated) provided within the ultrasonic endoscope 12, is provided on the upper surface of the ultrasonic oscillator array 100 and on the surface that is not covered with the acoustic matching layer 96 and is covered only with the acoustic lens 94.

Here, as long as positions where the respective oscillator electrodes 103 of the electrode part 104 of the ultrasonic oscillator array 100 are disposed is such that the workability in a case where wiring between the cable wiring part 88 and the electrode part 104 is performed is not impaired, the positions do not need to be a lower side of each side surface of the ultrasonic oscillator array 100 that is strictly perpendicular to the longitudinal direction of the plurality of ultrasonic oscillators 98. For that reason, in the invention, the expression "perpendicular to the arrangement surface of the plurality of ultrasonic oscillators 98 that constitute the ultrasonic oscillator array 100" means perpendicular or substantially perpendicular (90 degrees) with an accuracy within a range of minus 5 degrees to plus 5 degrees with respect to the arrangement surface of the plurality of ultrasonic oscillators 98. Moreover, unless the wiring to the cable wiring part 88 becomes complicated, as illustrated in FIG. 4, the oscillator electrodes 103 do not need to be disposed on lower sides of both side surfaces of the ultrasonic oscillator array 100, and may be provided at least on one end surface perpendicular to the longitudinal direction of the plurality of ultrasonic oscillators 98.

Additionally, the plurality of ultrasonic oscillators 98 constituting the ultrasonic oscillator array 100 are constituted of piezoelectric elements, and have a configuration in which electrodes are formed on both surfaces a piezoelectric thick film, such as lead zirconium titanate or polyvinylidene fluoride. Additionally, as methods of electrical connection between the electrode part 104 the ultrasonic oscillator array 100 and the cable wiring part 88 and between the upper electrode part 106 and wiring lines, well-known methods, such as methods using wire bonding, soldering, heat welding, a anisotropic conductive sheet, and anisotropic conductive paste, can be used as long as the methods are methods that do not impair the workability of the wiring task.

In the ultrasonic oscillator unit 68 of the ultrasonic observation part 58, in a case where each ultrasonic oscillator 98 of the ultrasonic oscillator array 100 of the laminated body 86 to be described below is driven and a voltage is applied to both the electrodes of the electrode part 104 and the upper electrode part 106 of the ultrasonic oscillator 98, piezoelectric bodies oscillate to sequentially generate the ultrasonic waves, and the ultrasonic waves are radiated toward the region to be observed of the subject. Then, by sequentially driving the plurality of ultrasonic oscillators 98 using an electronic switch, such as a multiplexer, scanning is performed with the ultrasonic waves within a scanning range along a curved surface on which the ultrasonic oscillator array 100 is arranged, for example, within a range of about several tens of mm from the center of curvature of the curved surface.

Additionally, in a case where the echo signals (ultrasound echoes) reflected from the region to be observed are received, the piezoelectric bodies oscillate to generate voltages, and the voltages are output to the ultrasonic wave processor device 14 as electrical signals (ultrasonic detection signals) according to the received ultrasound echoes. After various kinds of signal processing are performed in the ultrasonic wave processor device 14, the ultrasonic detection signals are displayed as the ultrasound image on the monitor 20.

The backing material layer 102 of the laminated body 86 mechanically supports the ultrasonic oscillator array 100, suppresses the oscillation of the ultrasonic oscillator array 100, and damps the ultrasonic waves propagated to the lower side of the ultrasonic oscillator array 100, is disposed such that the upper surface of the backing material layer 102 abuts against the lower surface of the ultrasonic oscillator array 100, and has a width longer than the ultrasonic oscillator array 100 in the width direction of the laminated body 86. In addition, the backing material layer 102 is configured using a material having rigidity, such as hard rubber, and an ultrasonic damping material made of, for example, ferrite or ceramics, is added as needed.

The electrode part 104, which includes the oscillator electrodes 103 disposed on the lower sides of both side surfaces of the ultrasonic oscillator array 100 that are perpendicular to the longitudinal direction of the plurality of ultrasonic oscillators 98 constituting the ultrasonic oscillator array 100, is electrically connected to the plurality of oscillator connecting terminals 109 of the oscillator connecting part 107 of the cable wiring part 88. The electrode part 104 is used to transmit the driving signals of the ultrasonic waves from the ultrasonic wave processor device 14 of the ultrasonic inspection system 10, to the ultrasonic oscillator array 100 via the cables 70 of the cable dispersion part 72, and to transmit the piezoelectric signals output after the ultrasonic oscillator array 100 receives the reflected ultrasonic waves, via the cables 70 to the ultrasonic wave processor device 14 that performs the analysis of the received ultrasonic signals and the creation of the ultrasound image. In this way, since the electrode part 104 is a structure disposed on each side surface of the ultrasonic oscillator array 100, wiring to the electrode part 104 can be relatively easily performed, and the success rate of manufacture of the laminated body 86. In addition, as methods of electrical connection between the cable wiring part 88 and the cables 70, well-known methods, such as methods using wire bonding, soldering, heat welding, a anisotropic conductive sheet, and anisotropic conductive paste, can be used as long as the methods are methods that do not impair the workability of the wiring task. Additionally, the electrode part 104 may be provided such that the cable wiring part 88 is disposed along each side surface of the backing material layer 102 in the width direction thereof, that is may be provided on an end surface side of the ultrasonic oscillator array 100 that is perpendicular to the arrangement surface of the plurality of ultrasonic oscillators 98, or may be connected to one end of the cable wiring part 88 and each side surface of the backing material layer 102 in the width direction thereof by being provided to extend to an upper end part of each side surface of the backing material layer 102 in the width direction thereof.

The upper electrode part 106, which is disposed on the surface that is an upper surface of the ultrasonic oscillator array 100, is not covered with the acoustic matching layer 96, and is covered only with the acoustic lens 94, is electrically connected to the grounding electrode (not illustrated) that includes one electrode pad connected to the plurality of respective ultrasonic oscillators 98 that constitute the ultrasonic oscillator array 100, and is provided within the ultrasonic endoscope 12, and is used to ground the driving signals for oscillating the ultrasonic waves, which are transmitted from the ultrasonic wave processor device 14 and transmitted from the electrode part 104 disposed on the lower side of each side surface of the ultrasonic oscillator array 100 to the respective ultrasonic oscillators 98 constituting the ultrasonic oscillator array 100, through the grounding electrode provided within the ultrasonic endoscope 12. Additionally, the upper electrode part 106 is disposed on the upper surface of the ultrasonic oscillator array 100. However, as described above, since the upper electrode part 106 is disposed in the region outside each side surface of the acoustic matching layer 96 in the width direction thereof, there is no particular influence on the transmission and reception of ultrasonic waves performed by the ultrasonic oscillator array 100. In addition, the upper electrode part 106 only has to be capable of grounding the plurality of respective ultrasonic oscillators 98 constituting the ultrasonic oscillator array 100, and it is needless to say that the upper electrode part 106 is not necessarily constituted of one electrode pad as long as the working efficiency of the wiring task in the upper electrode part 106 is not hindered.

As described above, in the invention, the plurality of cables 70 of the cable dispersion part 72 are respectively wired to the plurality of strip-like electrode parts 111 of the cable connecting part 108 disposed along the staircase part 92 formed in the stepwise fashion. Thus, the plurality of cables 70 and the plurality of strip-like electrode parts 111 can be wired efficiently using the space within the endoscope distal end part 40 such that the plurality of cables 70 do not come into contact with each other. For that reason, in the cable wiring part 88, the workability in wiring to the plurality of cables 70 and the plurality of strip-like electrode parts 111 can be improved using the electrode arrangement of a simple configuration, and the success rate in a case where the ultrasonic oscillator unit 68 is manufactured can be improved, and the ultrasonic oscillator unit can be made small-sized.

In addition, in the above-described example, the staircase part 92 is provided on the center side of the backing material layer 102 in the width direction thereof and the electrode pads 112 of the strip-like electrode parts 111 of the cable wiring part 88 are disposed in a stepwise fashion on both sides of the staircase part 92 in the width direction thereof. However, the invention is not limited to this, and the staircase part 92 may be provided on the center side of the backing material layer 102 in the width direction thereof, and the electrode pads 112 of the strip-like electrode parts 111 of the cable wiring part 88 may be disposed in a stepwise fashion.

Additionally, as long as the staircase part 92 can support the plurality of strip-like electrode parts 111 of the cable wiring part 88 in a stepwise fashion, the staircase part 92 is not particularly restrictive, and may not be an integral member or may be constituted of a plurality of strip-shaped supporting members having different thicknesses.

Although the invention has been described above in detail, it is natural that the invention is not limited to the above embodiment, and various improvements and modifications may be made without departing from the scope of the invention.

EXPLANATION OF REFERENCES

10: ultrasonic inspection system
12: ultrasonic endoscope
14: ultrasonic wave processor device
16: endoscope processor device
18: light source device
20: monitor
22: water supply tank
24: suction pump
26: insertion part
28: operating part 30: universal cord
32: air/water supply button
34: suction button
36: angle knob
38: treatment tool insertion port
40: endoscope distal end part
42: bending part
44: flexible part
46: ultrasonic wave connector
48: endoscope connector
50: light source connector
52a, 52b: tube
54: inclined surface part
56: endoscope observation part
58: ultrasonic observation part
60: treatment tool delivery port
61: treatment tool insertion channel
62: air/water supply nozzle
64: imaging unit
66: illumination unit
68: ultrasonic oscillator unit
70: cable
72: cable dispersion part
74: cable covering part
76: observation window
78: objective lens
80: imaging element
82: signal cable
84: illumination window
86: laminated body
88: cable wiring part
90: housing
92: staircase part
93: filler layer
94: acoustic lens
96: acoustic matching layer
98: ultrasonic oscillator
100: ultrasonic oscillator array
102: backing material layer
103: oscillator electrode
104: electrode part
106: upper electrode part
107: oscillator connecting part
108: cable connecting part
109: oscillator connecting terminal
110: belt-like piece
111: strip-like electrode part
112: electrode pad
113a: first bent part
113b: second bent portion

What is claimed is:
1. An ultrasonic oscillator unit comprising:
an ultrasonic oscillator array in which a plurality of ultrasonic oscillators having a rod shape are arranged in a circular-arc shape while aligning in a longitudinal direction of the rod shape;
an electrode part that is provided on at least one end surface of the plurality of ultrasonic oscillators perpendicular to the longitudinal direction and has a plurality of electrodes electrically connected to the plurality of ultrasonic oscillators, respectively;
a circular-arc backing material layer that is disposed on a rear surface of the ultrasonic oscillator array that becomes a center side of the circular-arc shape; and
a cable wiring part including a flexible printed wired board in which a plurality of cables are disposed at a plurality of wiring lines electrically connected to the plurality of electrodes of the electrode part,
wherein the flexible printed wired board extends to a lower side of the backing material layer that becomes a side opposite to the ultrasonic oscillator array and are separated into a plurality of belt-like pieces in a comb shape,
wherein the cable wiring part has a cable connecting part including, in a comb shape, a plurality of strip-like electrode parts that are provided in the plurality of belt-like pieces, and
wherein each of the strip-like electrode parts is formed by linearly disposing at least one electrode pad in a longitudinal direction of each of the belt-like pieces on each belt-like piece.
2. The ultrasonic oscillator unit according to claim 1, further comprising:
a staircase part that is disposed to abut against a lower surface of the backing material layer, is perpendicular to a width direction of the backing material layer along the longitudinal direction of the rod shape, and becomes stepwise in the width direction of the backing material layer from an ultrasonic oscillator side at one end part of the ultrasonic oscillator array toward an ultrasonic oscillator side on the other end part thereof with respect to the lower surface of the backing material layer,
wherein a portion above the cable connecting part of the cable wiring part is disposed along the backing material layer,
wherein the plurality of belt-like pieces of the flexible printed wired board are bent along the lower surface of the backing material layer, are bent at respective steps of the staircase part again, and are disposed along the respective steps of the staircase part, and
wherein the plurality of strip-like electrode parts of the cable connecting part are respectively disposed on the belt-like pieces disposed along the respective steps of the staircase part.
3. The ultrasonic oscillator unit according to claim 2, wherein the cable connecting part has the same number of strip-like electrode parts as the number of the steps of the staircase part.
4. The ultrasonic oscillator unit according to claim 2, wherein a width of the plurality of strip-like electrode parts is narrower than a width, in a step difference direction, of the respective steps of the staircase part along which the strip-like electrode parts are respectively disposed.
5. The ultrasonic oscillator unit according to claim 3, wherein a width of the plurality of strip-like electrode parts is narrower than a width, in a step difference direction, of the respective steps of the staircase part along which the strip-like electrode parts are respectively disposed.
6. The ultrasonic oscillator unit according to claim 2, wherein lengths of the respective strip-like electrode parts in a longitudinal direction thereof are longer as the strip-like electrode parts are disposed along lower steps of the staircase part, and the numbers of the electrode pads of the respective strip-like electrode parts are larger as the electrode pads are disposed along the lower steps of the staircase part.
7. The ultrasonic oscillator unit according to claim 3, wherein lengths of the respective strip-like electrode parts in a longitudinal direction thereof are longer as the strip-like electrode parts are disposed along lower steps of the staircase part, and the numbers of the electrode pads of the respective strip-like electrode parts are larger as the electrode pads are disposed along the lower steps of the staircase part.

8. The ultrasonic oscillator unit according to claim 4, wherein lengths of the respective strip-like electrode parts in a longitudinal direction thereof are longer as the strip-like electrode parts are disposed along lower steps of the staircase part, and the numbers of the electrode pads of the respective strip-like electrode parts are larger as the electrode pads are disposed along the lower steps of the staircase part.

9. The ultrasonic oscillator unit according to claim 5, wherein lengths of the respective strip-like electrode parts in a longitudinal direction thereof are longer as the strip-like electrode parts are disposed along lower steps of the staircase part, and the numbers of the electrode pads of the respective strip-like electrode parts are larger as the electrode pads are disposed along the lower steps of the staircase part.

10. The ultrasonic oscillator unit according to claim 2, wherein in the cable connecting part, the plurality of cables are wired so as to be directed from higher steps of the staircase part to lower steps thereof, using the electrode pads of each of the strip-like electrode parts as one end.

11. The ultrasonic oscillator unit according to claim 3, wherein in the cable connecting part, the plurality of cables are wired so as to be directed from higher steps of the staircase part to lower steps thereof, using the electrode pads of each of the strip-like electrode parts as one end.

12. The ultrasonic oscillator unit according to claim 4, wherein in the cable connecting part, the plurality of cables are wired so as to be directed from higher steps of the staircase part to lower steps thereof, using the electrode pads of each of the strip-like electrode parts as one end.

13. The ultrasonic oscillator unit according to claim 5, wherein in the cable connecting part, the plurality of cables are wired so as to be directed from higher steps of the staircase part to lower steps thereof, using the electrode pads of each of the strip-like electrode parts as one end.

14. The ultrasonic oscillator unit according to claim 6, wherein in the cable connecting part, the plurality of cables are wired so as to be directed from higher steps of the staircase part to lower steps thereof, using the electrode pads of each of the strip-like electrode parts as one end.

15. The ultrasonic oscillator unit according to claim 7, wherein in the cable connecting part, the plurality of cables are wired so as to be directed from higher steps of the staircase part to lower steps thereof, using the electrode pads of each of the strip-like electrode parts as one end.

16. The ultrasonic oscillator unit according to claim 8, wherein in the cable connecting part, the plurality of cables are wired so as to be directed from higher steps of the staircase part to lower steps thereof, using the electrode pads of each of the strip-like electrode parts as one end.

17. The ultrasonic oscillator unit according to claim 9, wherein in the cable connecting part, the plurality of cables are wired so as to be directed from higher steps of the staircase part to lower steps thereof, using the electrode pads of each of the strip-like electrode parts as one end.

18. The ultrasonic oscillator unit according to claim 2, wherein the respective steps of the staircase part have a width wider than the strip-like electrode parts in the longitudinal direction of the strip-like electrode parts disposed along the steps and have wider width at lower steps.

19. The ultrasonic oscillator unit according to claim 3, wherein the respective steps of the staircase part have a width wider than the strip-like electrode parts in the longitudinal direction of the strip-like electrode parts disposed along the steps and have wider width at lower steps.

20. The ultrasonic oscillator unit according to claim 2, wherein the staircase part is made of the same material as that of the backing material layer.

\* \* \* \* \*